(12) United States Patent
Noiles et al.

(10) Patent No.: US 6,264,699 B1
(45) Date of Patent: Jul. 24, 2001

(54) MODULAR STEM AND SLEEVE PROSTHESIS

(75) Inventors: Douglas G. Noiles, New Canaan; Alfred F. DeCarlo, Jr., Stamford, both of CT (US)

(73) Assignee: Depuy Orthopaedics, Inc., New Brunswick, NJ (US)

( * ) Notice: Subject to any disclaimer, the term of this patent is extended or adjusted under 35 U.S.C. 154(b) by 0 days.

(21) Appl. No.: 09/197,854

(22) Filed: Nov. 23, 1998

(51) Int. Cl.[7] .................................................. A61F 2/32
(52) U.S. Cl. ..................... 623/23.23; 623/22.41; 623/22.42; 623/20.15
(58) Field of Search ............................ 623/18–23, 23.23, 623/23.35

(56) References Cited

U.S. PATENT DOCUMENTS

| | | | |
|---|---|---|---|
| 4,790,852 | 12/1988 | Noiles | 623/18 |
| 4,822,366 | 4/1989 | Bolesky | 623/20 |
| 4,878,917 * | 11/1989 | Kranz et al. | 623/18 |
| 4,936,853 | 6/1990 | Fabian et al. | 623/20 |
| 5,002,578 * | 3/1991 | Luman | 623/23 |
| 5,080,685 * | 1/1992 | Bolesky et al. | |
| 5,507,830 * | 4/1996 | DeMane et al. | 623/23 |
| 5,725,592 | 3/1998 | White et al. | 623/22 |
| 5,766,263 * | 6/1998 | Grundei et al. | 623/23 |
| 5,876,459 * | 3/1999 | Powell | 623/18 |

FOREIGN PATENT DOCUMENTS

| 0634154 | 1/1995 | (EP) | A61F/2/36 |
|---|---|---|---|

* cited by examiner

*Primary Examiner*—Bruce Snow

(57) ABSTRACT

An orthopaedic prosthesis system for replacement of an articulating portion of a long bone includes a sleeve, a stem, and a neck. The sleeve has an outer bone engagement surface and includes opposed proximal and distal female taper regions. The stem has a distal end for fixation within a long bone and a proximal end including a male taper region engaged with the distal female taper of the sleeve. The neck has a taper post that engages the proximal taper of the sleeve. Both the neck and the sleeve may define axial bores, the axial bore in the sleeve communicating with and being generally coaxial with the two opposed female tapers, and the neck axial bore extending through the taper post. A connecting element can engage the stem, pass through the axial bore in the sleeve, extend into the axial bore in the neck taper post, and engage the neck.

19 Claims, 8 Drawing Sheets

MODULAR STEM AND SLEEVE PROSTHESIS

CROSS-REFERENCE TO RELATED APPLICATIONS

Not Applicable.

STATEMENT REGARDING FEDERALLY SPONSORED RESEARCH

Not Applicable.

FIELD OF THE INVENTION

The present invention relates to a prosthesis for replacing an articulating portion of a long bone, the prosthesis having modular stem and sleeve components.

BACKGROUND OF THE INVENTION

Replacement of articulating joints in humans has become increasingly common. In the replacement of many articulating joints, it is necessary to implant a prosthesis within a long bone, the prosthesis completely replacing the articulating end of the bone. For example, a distal femoral element is often necessary when replacing a knee joint; a proximal femoral element for a hip joint; a proximal humeral element for a shoulder joint; etc.

Recently, modular prosthesis components for replacing the end of a long bone in joint replacement surgery have become more popular. Successful joint replacement surgery depends, in part, on careful selection of prosthesis components to replace portions of the patient's bone with components that properly fit with existing bone and restore natural function to the joint being replaced. In order to provide prostheses that would exactly fit each patient who might require joint replacement surgery, hospitals would have to inventory an extraordinary number of single piece prostheses. With single piece prostheses, the only other option is to stock fewer prostheses with the result that many patients will receive a prosthesis that fits well only in one aspect.

As an alternative, modular prosthesis components have been developed, such as the modular sleeve prosthesis of U.S. Pat. No. 4,790,852, or the modular stem, sleeve and neck combinations disclosed in U.S. Pat. Nos. 5,002,578 and 5,725,592. While improving the situation described above in some respects, existing modular prosthesis configurations may still be improved. For example, present designs do not allow for a single modular sleeve to engage a wide variety of stem sizes, requiring multiple sleeves of the same size for various different stem size combinations and increasing rather than decreasing inventory. Present modular sleeve designs do not allow for sleeves of varying lengths to be used modularly with existing stems while still providing a desired snug fit between prosthesis components. Extended length sleeves are particularly desirable when the joint replacement surgery is necessary due to cancer or some other degenerative bone disease or condition and greater filling of the long bone in proximity to the joint is desired. In addition, present designs do not provide all of these modularity advantages while providing for assembly of all the modular components within the patient—allowing the surgeon to align and properly fit each modular component separately and reducing the chances of malaligning or misfitting a component.

SUMMARY OF THE INVENTION

The present invention provides an orthopaedic prosthesis system for replacement of an articulating portion of a long bone including a sleeve, a stem, and a neck. The sleeve has an outer bone engagement surface and includes opposed proximal and distal female taper regions. The stem has a distal end for fixation within a long bone, and a proximal end including a male taper region that engages with the distal female taper of the sleeve. The neck has a taper post that engages the proximal female taper of the sleeve.

In one embodiment, both the neck and the sleeve define axial bores, the axial bore in the sleeve communicating with and being generally coaxial with the two opposed female tapers, and the neck axial bore extending through the taper post. A connecting element can engage the stem, pass through the axial bore in the sleeve, extend into the axial bore in the neck taper post, and engage the neck. Tightening the connecting element tightens the taper connections.

The prosthesis system may be highly modular, combining a neck, stem and sleeve selected from groups of components having different sizes and shapes. In addition, specific embodiments of the invention may be applied to different joint prostheses including, for example, hip, knee and shoulder prosthesis.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
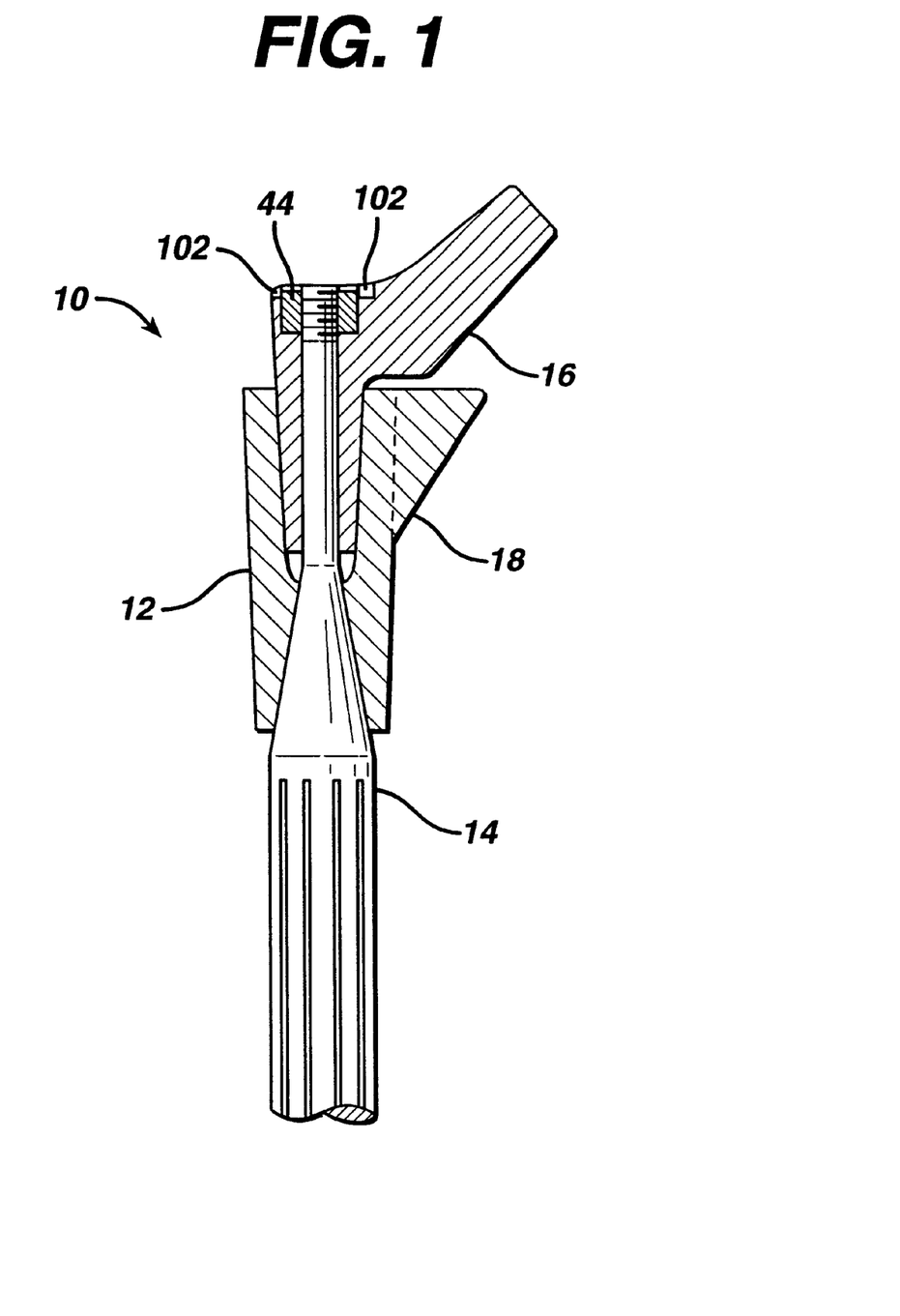
FIG. 1 is a side view, partly in section, of an orthopaedic prosthesis system of the invention having a sleeve, a stem, and a neck.

An orthopaedic prosthesis system 10 of the invention for replacing an articulating portion of a long bone having a sleeve 12, a stem 14 and a neck 16 is illustrated in FIG. 1. Sleeve 12, also shown in FIG. 2, has an outer bone engaging surface 18 and defines an axial bore 20 through the sleeve. Sleeve 12 has opposed proximal and distal female taper regions 22, 24 communicating with the axial bore 20. Proximal taper 22 starts at, or in proximity to, the proximal end 26 of sleeve 12 and extends into the sleeve tapering inward. Distal taper 24 starts at, or in proximity to, the distal end 28 of the sleeve 12 and tapers inward in a proximal direction. The taper regions 22, 24 may communicate directly with each other, or may communicate with a straight bore 30 that extends in coaxial fashion between the taper regions 22, 24.

Figure 2:
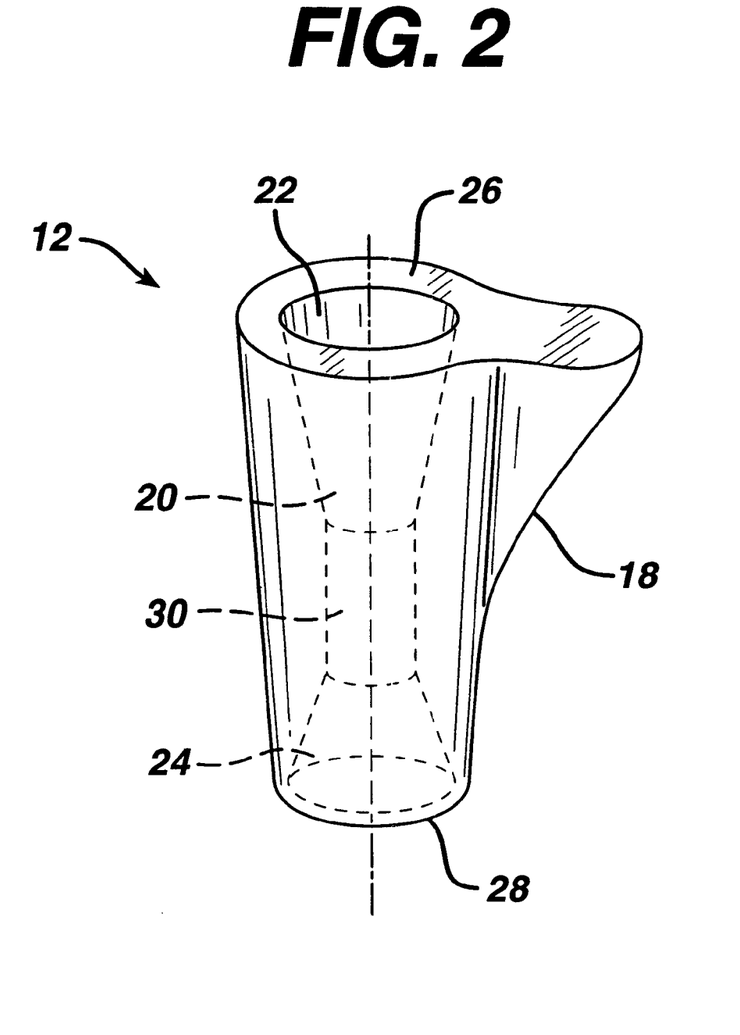
FIG. 2 is a perspective view of the sleeve of FIG. 1.

Sleeve 12 may be constructed from any material useful for permanent implantation as part of an articulating prosthesis and may preferably include titanium or a titanium alloy. The bone contacting surface 18 of sleeve 12 may have a surface finish appropriate to the desired relationship between the sleeve 12 and the surrounding bone. For example, the bone contacting surface may be porous coated to promote bone ingrowth, and it may include a series of terraces such as terraces 28 provided on sleeve 13 of U.S. Pat. No. 4,790,852 to Noiles which is hereby incorporated by reference. In addition, bone contacting surface 18 may be shaped to generally correspond to the inner surfaces of hard bone found in a long bone. U.S. Pat. No. 4,790,852 provides examples of such a shape for a proximal femur to which the prosthesis system of the invention might be fixed in a total hip arthroplasty.

Proximal and distal taper regions 22, 24 are generally configured with about a three degree taper per side, commonly referred to as a Morse type self-locking taper, however, other configurations may be used consistent with the spirit of the invention.

Figure 3:
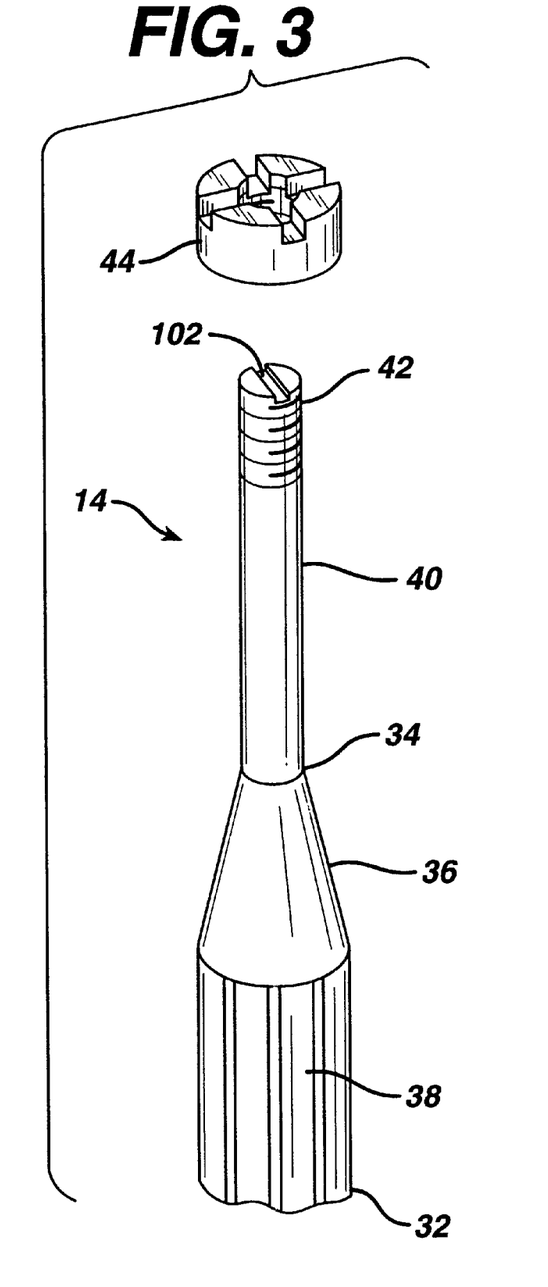
FIG. 3 is a perspective view of the stem of FIG. 1.

Stem 14, also shown in FIG. 3, has a distal end 32 for fixation within a long bone and a proximal end 34 having a taper region 36. The distal end 32 of stem 14 may include a variety of bone fixation elements including flutes 38 and/or one or more distal slots (not shown). Taper region 36 is configured to mate with the distal taper region 24 of sleeve 12. Stem 14 may be formed from the same materials as sleeve 12.

Figure 4:
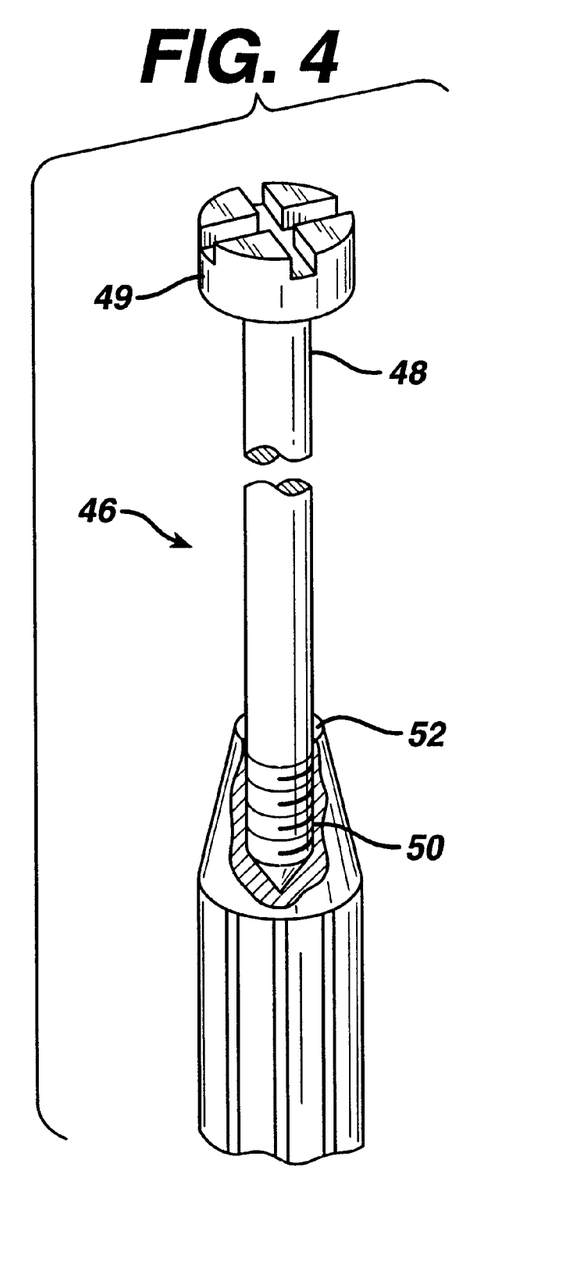
FIG. 4 is a perspective view of an alternative stem useful with the prosthesis of FIG. 1.

Stem 14 may also have a connecting element 40 affixed to its proximal end 34 so as to extend through the axial bore 20 of sleeve 12 to attach to neck 16 upon assembly of prosthesis is 10. Connecting element 40 includes an extending connecting rod integral with the stem proximal end 34 and a threaded proximal end 42. A nut 44 (FIG. 1) may be provided on the threaded proximal end 42 of connecting element 40 to attach the connecting element to neck 16. An alternative stem 46, shown in FIG. 4, is used with a screw 48 that extends through neck 16 and axial bore 20 of sleeve 12 to engage a threaded opening 50 in the proximal end 52 of stem 46. While other mechanisms may be employed to fasten the prosthesis system of the invention, the connecting element will preferably be accessible to the surgeon during implantation for tightening so that tightening the connecting element forces the two opposed taper interlocks together to affirmatively fix the prosthesis components to each other.

Figure 5:
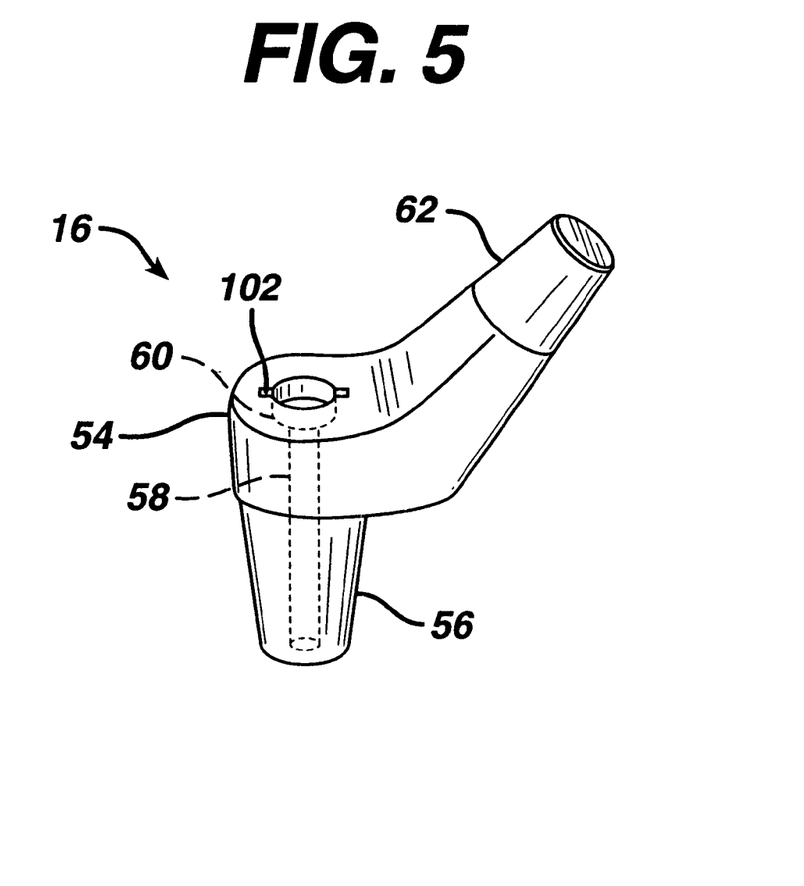
FIG. 5 is a perspective view of the neck of FIG. 1.

Neck 16, also illustrated in FIG. 5, includes a body 54 having a taper post 56 extending distally therefrom and configured to mate with the proximal female taper 22 of sleeve 12. Neck 16 defines an axial through bore 58 extending through taper post 56 and body 54. The wall of the axial bore 58 may also define a seat 60 for a connecting element such as nut 44 or head 49 of screw 48. Neck 16 may include an articulating surface integrally formed thereto or it may include a modular articulation element. Neck 16 has a second taper post 62 which can be used to attach a modular articulating element such as a head member for a total hip arthroplasty.

The configuration of prosthesis system 10, and in particular the configuration of sleeve 12 having opposed tapers 22, 24, provides greater modularity with fewer parts than is possible using known prosthesis designs. For example, known modular designs typically require multiple sleeves, not only for each desired outer, bone contacting diameter, but also having different inside diameters or taper sizes for each stem diameter. Accordingly, assuming nine different modular sleeve sizes for a particular implant, and 11 different stem diameters used with that same prosthesis, 99 sleeves would have to be stocked to allow for all possible combinations in the prosthesis system. With the present invention, fewer sleeves would need to be inventoried because distal taper 24 in sleeve 12 can be configured to attach a variety of stem diameters.

Figure 6:
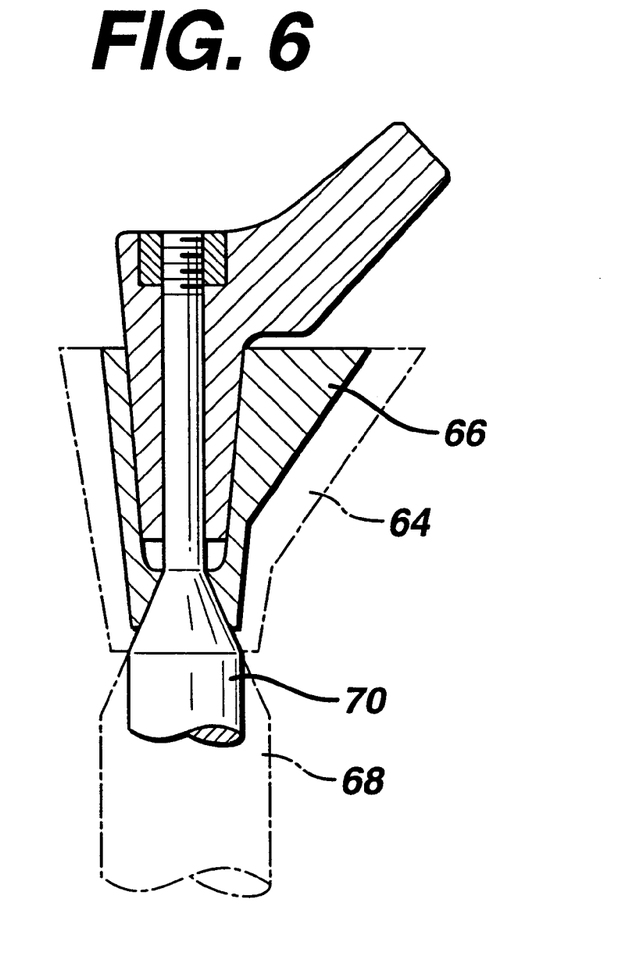
FIG. 6 is a diagrammatic view of an orthopaedic prosthesis system of the invention illustrating various sizes of stems and necks fitting together.

Even stems having a larger outer diameter than the sleeve may be modularly employed using the prosthesis system of the invention. FIG. 6 illustrates how large and small size sleeves 64, 66 modularly interact with large and small diameter stems 68, 70 in the prosthesis system of the invention. In particular, stem 68 may readily be used in combination with sleeve 66 which has a significantly smaller outer diameter than stem 68. Such a prosthesis is particularly useful where a maximum distal portion is desired, including, for example, use with bone allograft constructs.

Figure 7A:
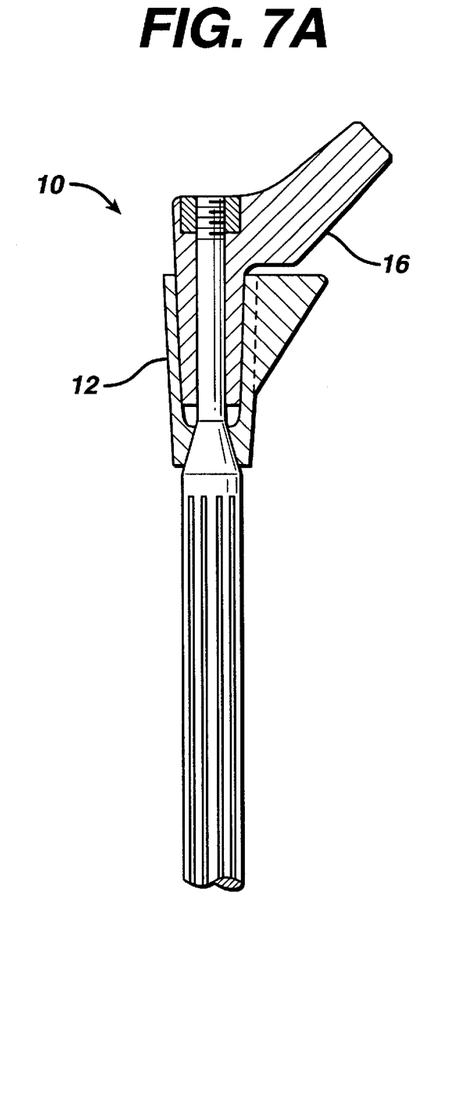
FIGS. 7A–B are side views, partly in section, of orthopaedic prostheses of the invention having sleeves of different lengths.
Figure 7B:
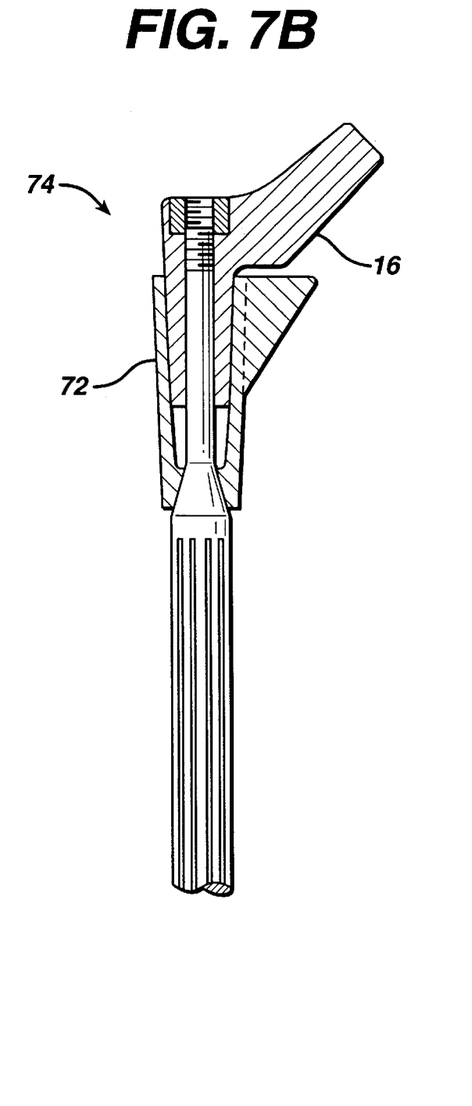

Sleeve 12 also provides modularity of sleeve length. Because of its configuration, sleeve 12 may be of any length desired and will still fit tightly to a stem. FIGS. 7A and 7B illustrate the effects of sleeve length on the prosthesis of the invention. Sleeve 12, shown in FIG. 7A with the prosthesis system 10 of the invention, is of "standard" length. Sleeve 72, shown in FIG. 7B with an alternate prosthesis system 74 of the invention, has an extended length, but combines with the same neck 16 and stem 14 components as sleeve 12 to form a prosthesis system of the invention. The ability to employ such extended sleeves modularly is particularly useful where the prosthesis replaces bone that has been damaged by cancer or some other disease or degenerative condition. This modularity of sleeve length allows for highly specialized prostheses while only having to stock additional sleeves rather than entire prostheses.

In FIG. 7B, due to the extended length of sleeve 72, the connecting element 40 only partially engages nut 44. If full engagement with nut 44 is desired, extended length sleeve 72 may be provided with an enlarged distal taper, allowing the stem to seat more deeply into the distal taper and reaching the full extent of nut 44 while maintaining the desired modularity of sleeve and stem size.

Figure 8A:
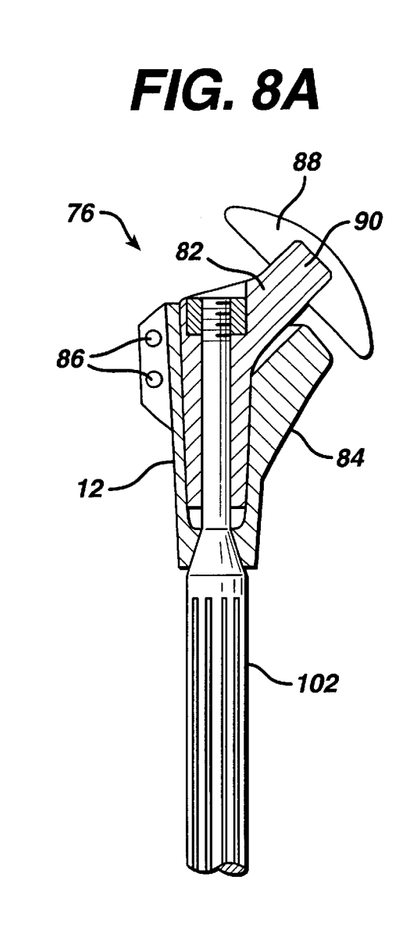
FIGS. 8A–C illustrate prosthesis systems of the invention configured to replace shoulder, knee and hip joints, respectively.
Figure 8B:
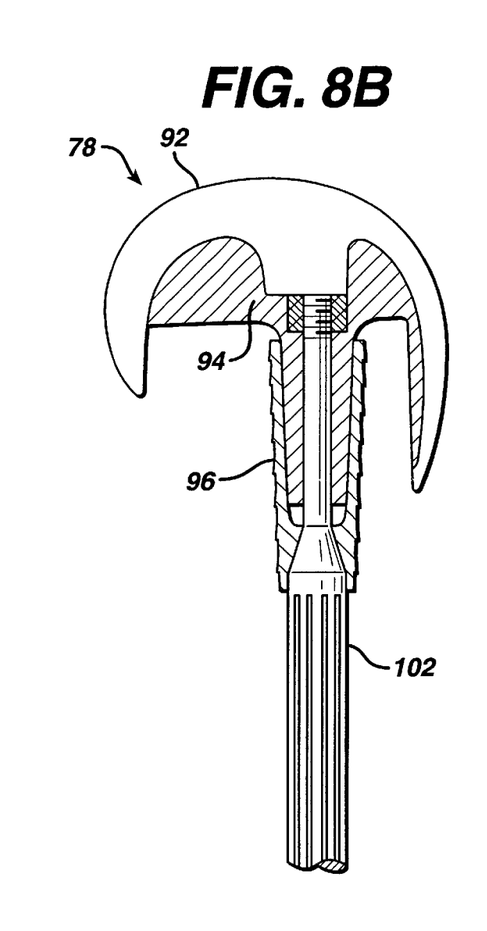
Figure 8C:
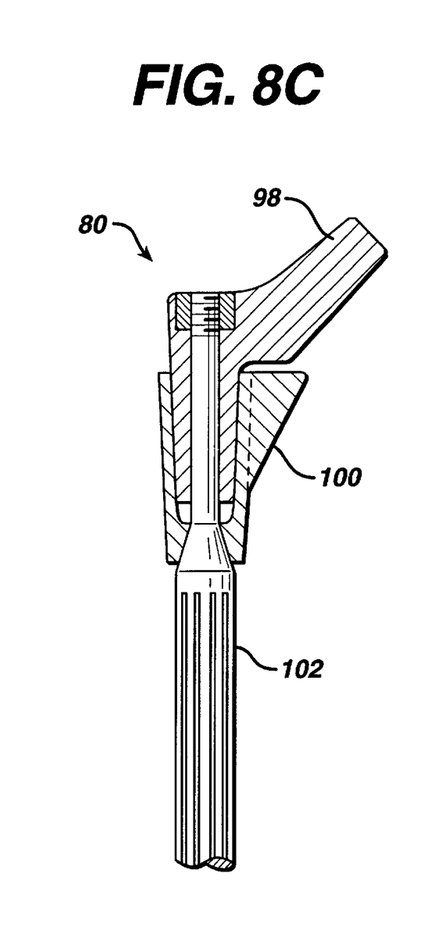

FIGS. 8A–C illustrate three prostheses of the invention adapted for implantation in the humerus (shoulder prosthesis 76), distal femur (knee prosthesis 78), and proximal femur (hip prosthesis 80). Shoulder prosthesis 76 includes a neck 82 and a sleeve 84 configured to fill the medullary canal of the proximal humerus and having connecting holes 86 for attaching soft tissue. A modular humeral head element 88 is attached to a taper post 90 on neck 82 for glenoid articulation. Knee prosthesis 78 includes a condylar articulation element 92 integral with neck 94 and a sleeve 96 configured to fill the medullary canal of the distal femur. Hip prosthesis 80 has a taper post 98 for attachment of a modular head, typically for articulation with a prosthetic acetabular component. Hip prosthesis 80 also includes a sleeve 100 designed to fill the medullary canal of the proximal femur. Each prosthesis 76, 78, 80 may use the same stem 102. Accordingly, where stem sizes overlap among the different types of prostheses of the invention, the number of stems kept in inventory may be reduced.

A prosthesis system 10 of the invention may be applied in a total hip arthroplasty by first preparing the proximal femur for receipt of a femoral endoprosthesis. Such preparation generally involves resecting the proximal neck and head of the femur and reaming the medullary canal. An exemplary procedure for preparing a proximal femur is provided in the description accompanying FIGS. 4–11 of U.S. Pat. No. 4,790,852, the disclosure of which has been incorporated by reference herein.

Modular prosthesis components are then selected from a group of prosthesis components for implantation. Stems, such as stem 14 (FIG. 3), for use in proximal femoral fixation generally range in size from 9 to 19 mm in diameter and from 110 up to 325 mm in length. Typically, stems are available in diameter sizes 2 mm apart, such as 9, 11, 13, 15, 17 and 19 mm, and lengths qualitatively characterized as standard, long and extra long. Each stem should have a similarly configured taper region 36 so that any stem chosen from a group of stems will mate with the distal female taper 24 of a sleeve 12. Stems for use with other joint endoprostheses, such as knee or shoulder prostheses, will be similarly configured but may include additional sizes. Accordingly, a stem for a variety of endoprostheses may be selected from a single group of stems.

Alternatively, patient weight and activity may require that stem tapers 36, as well as sleeve tapers 24 and connecting members 40 and 48, be available in two or three groups of stock sizes.

A modular sleeve, such as sleeve 12 (FIG. 2) may also be selected from a group of sleeves. While it is possible to design sleeves of a generic shape, generally the sleeves will be shaped to fill the medullary canal at the end of the long bone in which they are placed. Sleeves for a single application, such as a femoral endoprosthesis for hip surgery, are generally available in about 20 or more different sizes. With the increased modularity provided by the prosthesis system of the invention, additional sleeve sizes or configurations, such as extra long sleeves for example, may be employed. The distal female taper 24 should be configured to properly mate with a number of, or even all of, the possible stems that could be selected as part of the prosthesis.

A neck element, such as neck 16 (FIG. 5), may also be selected from a group of modular neck elements. For a typical modular femoral endoprosthesis used in a total hip arthroplasty, approximately six differently sized or configured neck elements are available. Typical variables include length of the neck, angle of the neck, and lateral offset of the angled portion from the stem. The group of modular neck elements may also include neck elements designed to replace the proximal humerus, distal femur or proximal tibia.

Once selected, the prosthesis components may be assembled outside the patient, or to reduce the possibility of misalignment, can be implanted component by component and tightened to form the final prosthesis construct within the patient.

Where the prosthesis is tightened within the patient, features may be provided to prevent twisting or torque during tightening. For example, an anti-rotation 102 slot can be provided on neck 16 (FIG. 5), or on connecting element 40 (FIG. 3) so that a torque wrench tightening a nut to tighten the prosthesis construct can do so while holding the neck and/or the stem against rotation.

It will be understood that the foregoing is only illustrative of the principles of the invention, and that various modifications of the disclosed orthopaedic reaming system, including combining features of the various disclosed embodiments, can be made by those skilled in the art without departing from the scope and spirit of the invention. All references cited herein are expressly incorporated by reference in their entirety.

What is claimed is:

1. An orthopaedic prosthesis system for replacement of an articulating portion of a long bone comprising:

a sleeve having an outer bone engagement surface and defining an axial bore though the sleeve, the bore including opposed proximal and distal female taper regions, a stem having a distal end for fixation within a long bone and a proximal end including a male taper region engaged with the distal female taper of the sleeve;

a neck having an articulating portion connecting element and a distal taper post, the neck defining an axial bore through the neck and extending through the distal taper post, the distal taper post being engaged with the proximal taper of the sleeve; and a connecting element engaged with the proximal end of the stem, extending through the axial bore in the sleeve, extending into the axial bore in the neck and engaging the neck, the connecting element being tightenable from the neck.

2. The orthopaedic prosthesis system of claim 1, wherein the system further comprises a kit including a plurality of sleeves having different sizes;

a plurality of necks having different sizes; and a plurality of stems having different sizes;

wherein the sleeve is selected from the plurality of sleeves having different sizes, and the neck is selected from the plurality of necks having different sizes, and the stem is selected from the plurality of stems having different sizes.

3. The orthopaedic prosthesis system of claim 2, wherein the distal female taper region of each sleeve in the group of sleeves and the taper region of each stem in the group of stems are sized so that a sleeve selected from the group of sleeves is engageable with a plurality of stems of the group of stems having different sizes.

4. The orthopaedic prosthesis system of claim 3, wherein a sleeve selected from the group of sleeves is engageable with a stem selected from the group of stems, the stem having a greater outer diameter than the sleeve.

5. The orthopaedic prosthesis system of claim 2, wherein the group of sleeves includes sleeves having different lengths.

6. The orthopaedic prosthesis system of claim 2, wherein the group of sleeves includes sleeves configured to fit a medullary canal of at least one of the group consisting of a proximal femur, a proximal humerus and a distal femur.

7. The orthopaedic prosthesis system of claim 2, wherein the group of sleeves includes at least one sleeve configured to fit a medullary canal of one of the group consisting of a proximal femur, a proximal humerus and a distal femur, and further includes at least one sleeve configured to fit a medullary canal of a second one of the group consisting of a proximal femur, a proximal humerus and a distal femur.

8. The orthopaedic prosthesis system of claim 2, wherein the group of sleeves includes at least one sleeve configured to fit a medullary canal of a proximal femur, at least one sleeve configured to fit a medullary canal of a proximal humerus, and at least one sleeve configured to fit a medullary canal of a distal femur.

9. The prosthesis system of claim 1, wherein the connecting element is threaded.

10. The prosthesis system of claim 9, wherein the connecting element comprises a connecting rod integral with the stem having a threaded proximal end and a nut seated in the neck.

11. The prosthesis system of claim 9, wherein the connecting element comprises a threaded screw seated in the neck and being threaded into the proximal end of the stem.

12. The prosthesis system of claim 9, further comprising an anti-rotation means formed on at least one of the proximal end of the connecting element and the neck in proximity to the axial bore.

13. An orthopaedic prosthesis system for replacement of an articulating portion of a long bone comprising:
- a plurality of sleeves having different sizes, each sleeve having an outer bone engagement surface and defining an axial bore though the sleeve, the bore including opposed proximal and distal female taper regions;
- a plurality of stems having different sizes, each stem having a distal end for fixation within a long bone and a proximal end including a male taper region engaged with the distal female taper of the sleeve; and
- a plurality of necks having different sizes, each neck having an articulating portion connecting element and a distal taper post, each neck defining an axial bore through the neck and extending through the distal taper post, the distal taper post being engaged with the proximal taper of the sleeve;
- wherein an implantable prosthesis is prepared by assembling a sleeve selected from the plurality of sleeves having different sizes, a neck selected from the plurality of necks having different sizes, and a stem selected from the plurality of stems having different sizes;
- the system further comprising a connecting element for the implantable prosthesis engaged with the proximal end of the stem, extending through the axial bore in the sleeve, extending into the axial bore in the neck and engaging the neck, the connecting element being from the neck.

14. The orthopaedic prosthesis system of claim 13, wherein the distal female taper region of each sleeve in the group of sleeves and the taper region of each stem in the group of stems are sized so that a sleeve selected from the group of sleeves is engageable with a plurality of stems of the group of stems having different sizes.

15. The orthopaedic prosthesis system of claim 14, wherein a sleeve selected from the group of sleeves is engageable with a stem selected from the group of stems, the stem having a greater outer diameter than the sleeve.

16. The orthopaedic prosthesis system of claim 13, wherein the group of sleeves includes sleeves having different lengths.

17. The orthopaedic prosthesis system of claim 13, wherein the group of sleeves includes sleeves configured to fit a medullary canal of at least one of the group consisting of a proximal femur, a proximal humerus and a distal femur.

18. The orthopaedic prosthesis system of claim 13, wherein the group of sleeves includes at least one sleeve configured to fit a medullary canal of one of the group consisting of a proximal femur, a proximal humerus and a distal femur, and further includes at least one sleeve configured to fit a medullary canal of a second one of the group consisting of a proximal femur, a proximal humerus and a distal femur.

19. The orthopaedic prosthesis system of claim 13, wherein the group of sleeves includes at least one sleeve configured to fit a medullary canal of a proximal femur, at least one sleeve configured to fit a medullary canal of a proximal humerus, and at least one sleeve configured to fit a medullary canal of a distal femur.

* * * * *

UNITED STATES PATENT AND TRADEMARK OFFICE
CERTIFICATE OF CORRECTION

PATENT NO. : 6,264,699 B1
DATED : July 24, 2001
INVENTOR(S) : Douglas G. Noiles and Alfred F. DeCarlo, Jr.

It is certified that error appears in the above-identified patent and that said Letters Patent is hereby corrected as shown below:

Column 6,
Line 22, delete the word "and"

Column 7,
Line 27, insert -- tightenable -- after the word "being"

Signed and Sealed this

Tenth Day of September, 2002

Attest:

JAMES E. ROGAN
Attesting Officer     Director of the United States Patent and Trademark Office